United States Patent [19]

Hitzel et al.

[11] 4,315,940
[45] Feb. 16, 1982

[54] ANTIDIABETIC 1-PIPERIDINE-SULFONYLUREAS

[75] Inventors: Volker Hitzel, Hofheim am Taunus; Rudi Weyer, Kelkheim; Karl Geisen, Frankfurt am Main; Günter Regitz, Bad Soden am Taunus, all of Fed. Rep. of Germany

[73] Assignee: Hoechst Aktiengesellschaft, Frankfurt am Main, Fed. Rep. of Germany

[21] Appl. No.: 211,331

[22] Filed: Nov. 26, 1980

[30] Foreign Application Priority Data

Dec. 1, 1979 [DE] Fed. Rep. of Germany ....... 2948434

[51] Int. Cl.³ .................. A61K 31/445; C07D 401/12
[52] U.S. Cl. .................................... 424/267; 424/258; 546/141; 546/200; 546/203; 546/205; 546/233; 546/246
[58] Field of Search .............................. 546/200, 141; 424/258,267

[56] References Cited

U.S. PATENT DOCUMENTS

| | | | |
|---|---|---|---|
| 3,709,908 | 1/1973 | Weber et al. ................ | 260/326.11 |
| 3,752,818 | 8/1973 | Plumpe et al. ................ | 546/200 X |
| 3,919,245 | 11/1975 | Weyer et al. .................. | 424/263 X |
| 3,987,174 | 10/1976 | Cotrel et al. .................. | 546/200 X |
| 4,000,287 | 12/1976 | Werner ........................... | 546/200 X |
| 4,029,795 | 6/1977 | Eichenberger et al. ........ | 546/141 X |

*Primary Examiner*—Richard A. Schwartz
*Attorney, Agent, or Firm*—Curtis, Morris & Safford

[57] ABSTRACT

Sulfonylureas of the formula

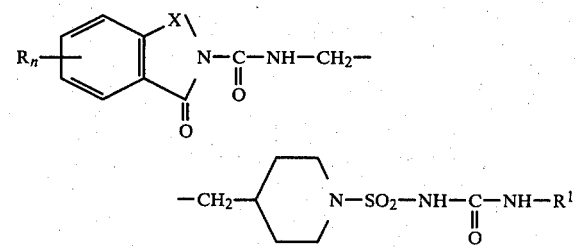

wherein n, R, R¹ and X have the indicated meanings, as well as their physiologically acceptable salts, pharmaceutical preparations on the basis of these compounds and their use for treating diabetes.

7 Claims, No Drawings

ANTIDIABETIC 1-PIPERIDINE-SULFONYLUREAS

The invention relates to sulfonylureas of the formula

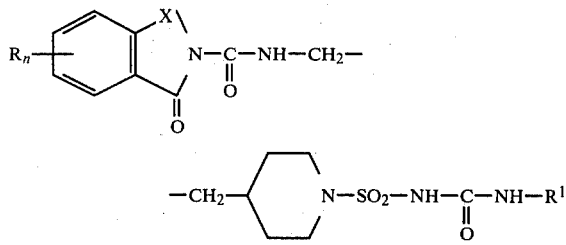

which, in substance or in the form of their physiologically acceptable salts, posses blood sugar-lowering properties and are distinguished by a pronounced and long-lasting lowering of the blood sugar level.

In the formula, the symbols have the following meanings:

n: 1 or 2,

R: hydrogen, alkyl with 1 to 4 carbon atoms, alkoxy with 1 to 4 carbon atoms or halogen which, with n being 2, may be identical or different, X: a —CH$_2$—, —CH$_2$—CH$_2$— or a —CH(CH$_3$)— group, R$^1$: alkyl of 2 to 8 C atoms, cycloalkyl, alkylcycloalkyl, dialkylcycloalkyl, cycloalkylalkyl, cycloalkenyl, or alkylcycloalkenyl, in each case with 5 to 9 C atoms, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

In the formula, R preferably denotes hydrogen, methyl, methoxy and halogen, especially chlorine. The particularly preferred meaning of R is hydrogen. X preferably denotes the —CH$_2$—group.

R$^1$ is preferably butyl, cyclohexyl, methylcyclohexyl; cyclohexyl is particularly preferred.

Bicyclic radicals are for example: bicyclo[2.2.1]-heptyl, bicyclo[2.2.1]heptylmethyl as well as the corresponding unsaturated radicals and the bicyclo[2.2.2]octyl radical.

The invention further relates to processes for the manufacture of these sulfonylureas, pharmaceutical preparations which contain these or consist of these compounds, and their use for the treatment of diabetes.

The processes of manufacture are characterized in that (a) 1-piperidine-sulfonyl-isocyanates, -carbamic acid esters, -thiolcarbamic acid esters, -ureas, -semicarbazides or -semicarbazones, which are substituted in the 4-position by the group

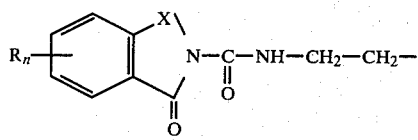

are reacted with an amine R$^1$—NH$_2$ or its salts, or sulfonamides of the formula

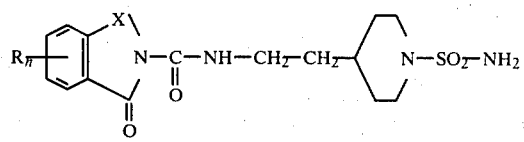

or their salts are reacted with R$^1$-substituted isocyanates, carbamic acid esters, thiolcarbamic acid esters, carbamic acid halides or ureas, (b) correspondingly substituted 1-piperidine-sulfonyl-iso-urea ethers, -isothiourea ethers, -parabanic acids or -halo-formic acid amidines are split, (c) in 1-piperidine-sulfonyl-thioureas substituted by

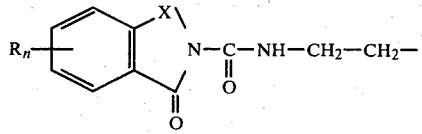

the sulfur atom is replaced by oxygen.

(d) the radical

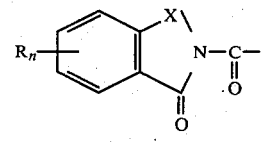

is introduced, optionally step by step, into 1-piperidine-sulfonylureas of the formula

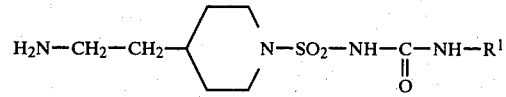

and the reaction products are optionally treated with alkaline agents for forming salts.

The 1-piperidine-sulfonyl-carbamic acid esters or -thiolcarbamic acid esters which have been mentioned can contain an alkyl radical or an aryl radical, or even a heterocyclic radical, in the alcohol component. Since this radical is split off during the reaction, its chemical structure has no influence on the character of the end product and can therefore be varied within wide limits. The same is true of the N-R$^1$-substituted carbamic acid esters or the corresponding thiocarbamic acid esters.

Suitable carbamic acid halides are above all the chlorides.

The 1-piperidine-sulfonylureas which may be used as starting materials for the process can be unsubstituted, monosubstituted or, in particular, disubstituted on the side of the urea molecule opposite from that carrying the sulfonyl group. Since these substituents are split off during the reaction with amines, their character can be varied within wide limits. In addition to alkyl-, aryl-, acyl- or heterocyclyl-substituted 1-piperidine-sulfonylureas it is also possible to use 1-piperidine-sulfonyl-carbamoylimidazoles and similar compounds or bis-piperidinesulfonylureas which on one of the nitrogen atoms can carry a further substituent, for example methyl. For example, such bispiperidinesulfonyl)-ureas or N-piperidinesulfonyl-N'-acylureas can be treated with R[1]-substituted amines and the resulting salts can be heated to elevated temperatures, especially to temperatures above 100° C.

Furthermore, it is possible to start from R[1]-substituted ureas, or from those R[1]-substituted ureas which are additionally monosubstituted or, in particular, disubstituted at the free nitrogen atom, and to react these with 1-piperidinesulfonamides substituted by

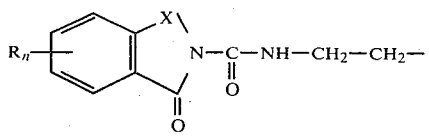

in the 4-position. Examples of possible starting materials of this type are N-cyclohexyl-urea, the corresponding N'-acetyl-, N'-nitro-, N'-cyclohexyl-, N',N'-diphenyl-, (it being possible for the two phenyl radicals also to be substituted and to be bonded to one another either directly or via a bridge member such as —CH$_2$—, —NH—, —O— or —S—), N'-methyl-N'-phenyl- and N',N'-dicyclohexyl-ureas as well as cyclohexyl-carbamoyl-imidazoles, -pyrazoles or -triazoles, and those of the compounds mentioned which instead of cyclohexyl carry some other substituent falling within the range of definition or R[1].

The scission of the 1-piperidinesulfonylparabanic acids, -isourea ethers, -isothiourea ethers or -haloformamidines mentioned as starting materials is advantageously effected by alkaline hydrolysis. Isourea ethers can also be very successfully subjected to scission in an acid medium.

The replacement of the sulfur atom in the thiourea grouping of correspondingly substituted 1-piperidinesulfonyl-thioureas by an oxygen atom can be effected in a known manner, for example with the aid of oxides or salts of heavy metals or by using oxidizing agents, such as hydrogen peroxide, sodium peroxide, nitrous acid or permanganates. The thioureas can also be desulfurized by treatment with phosgene or phosphorus pentachloride. Chloroformamidines of carbodiimides obtained as intermediates can be converted into the 1-piperidinesulfonylureas by suitable measures such as saponification or addition reaction with water.

The acylation of the sulfonylureas according to process (d) can be carried out with reactive derivatives of the acid

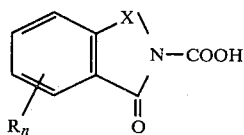

such as, for example, halides or urethanes.

The physiologically acceptable salts are manufactured in accordance with methods which are in themselves known. In particular, alkali metal and alkaline earth metal hydroxides, carbonates or bicarbonates, and physiologically tolerated organic bases, are suitable for forming salts.

The embodiments of the process according to the invention can, in general, be varied substantially in respect of the reaction conditions and be suited to the particular circumstances. For example, the reactions can be carried out in the absence or presence of solvents, at room temperature or at an elevated temperature.

Depending on the character of the starting materials, one or other of the processes described can, in some cases, give a desired individual 1-piperidinesulfonylurea only in low yields, or can be unsuitable for its synthesis. In such relatively rarely occuring cases it presents no difficulties to an expert to synthesize the desired product by another of the methods described.

The compounds obtained can be purified by dissolution and reprecipitation and/or recrystallization. Alternatively, purification is also possible by liberating the substance from a crystalline (alkali metal) salt by means of a suitable solvent.

The compounds according to the invention are distinguished by valuable pharmacological properties, especially blood sugar-lowering properties. The are therefore suitable for use as medicaments, especially as antidiabetics.

The blood sugar-lowering action of the piperidinesulfonyl-ureas described can be ascertained by feeding them as the free compounds, or in the form of the sodium salts in doses of 10 mg/kg or 2 mg/kg to rabbits which have received normal nutrition, and determining the blood sugar value by the known Hagedorn-Jensen method, or by means of an auto-analyzer, over a fairly long period of time.

However, the blood sugar-lowering effect can also be determined with lower doses or by other known methods.

N-Cyclohexyl-N'-(4-[2-(1-oxo-isoindoline-2-yl-carboxamido)-ethyl]-piperidinesulfonyl)-urea was orally administered to rabbits in doses of 2 mg/kg, and the lowering of the blood sugar was determined with an autoanalyzer over a fairly long time. After 1, 3, 6, 24 and 48 hours the lowering of the blood sugar was 24, 34, 35, 31 and 20%, respectively. Even 72 hours after administration the lowering was still 10%.

The acylureido-alkylpiperidinesulfonylureas according to the invention are distinguished by a pronounced and long-lasting blood sugar-lowering action.

The properties of the compounds make it possible to manage with such low doses in the therapy of diabetes mellitus that the preparation merely re-normalizes the reduced response capacity of the pancreas to an increased blood sugar level.

Benzenesulfonylureas containing a ureidoalkyl radical have already been described on several occasions (German OLS No. 1,443,911, German Auslegeschrift No. 1,670,700, German OLS Nos. 1,618,389 and 2,238,870). 1-Piperidinesulfonylureas containing an acylureidoalkyl radical were not previously known and it was not to be expected that they would be distinguished by the advantageous properties mentioned above.

The sulfonylureas described are preferentially intended for the manufacture of orally administrable preparations for the treatment of diabetes mellitus. They can be administered as such or in the form of their salts or in the presence of materials which lead to salt formation. For example, alkaline agents, such as alkali metal or alkaline earth metal hydroxides, carbonates or bicarbonates may be employed for forming salts. In addition to the sulfonylurea or its salt, the preparations can also contain other active compounds.

Suitable medicinal preparations are preferably tablets which in addition to the products of the process contain the customary excipients and auxiliaries such as talc, starch, lactose or magnesium stearate. A preparation which contains the described 1-piperidine-sulfonylureas as the active compound, for example a tablet or a powder, with or without additives, is advantageously converted to a suitably dosed form. The dose to be selected in this context is such as to suit the activity of the 1-piperidinesulfonylurea employed and to suit the desired effect. Advantageously, the dosage per unit is about 0.1 to 10 mg, preferably 0.5 to 2 mg, but dosage units above or below this, which may have to be divided before administration or of which several may have to be taken, can also be used.

The examples which follow show some of the numerous process variants which can be used for the synthesis of the sulfonylureas according to the invention. They are, however, not intended to imply a limitation of the subject of the invention.

EXAMPLE 1

N-cyclohexyl-N'-(4-[2-(1-oxo-isoindoline-2-yl-carboxamido)-ethyl]-piperidinesulfonyl)-urea 2.7 g of 4-(2-[2-(1-oxo-isoindoline-2-yl-carboxamido]-ethyl)-1-piperidine-sulfonamide are stirred for 3 hours in 50 ml of acetone and 25 ml of dioxan under reflux after addition of 2.1 g of ground potassium carbonate. After a short time of cooling, 1.05 g of cyclohexyl isocyanate dissolved in a small amount of acetone, are added dropwise and stirring is continued under reflux for another 5 hours. After cooling completely, the solution is diluted with water and acidified with 2 N hydrochloric acid. The precipitate is suction-filtered and recrystallized from ethanol. The N-cyclohexyl-N'-(4-[2-(1-oxo-isoindoline-2-yl-carboxamido)-ethyl]-piperidine-sulfonyl)-urea obtained melts at 176°-177° C.

The sulfonamide used as starting material is obtained by the following method:

1-Oxo-isoindoline-2-yl-carboxylic acid chloride (manufactured from 1-oxo-isoindoline-Na with phosgene) is reacted with 4-(2-amino-ethyl)-pyridine to give 4-(2-[1-oxo-iso-indoline-2-yl-carboxamido]-ethyl)-pyridine with a melting point of 158°-160° C. The 4-(2-[1-oxo-isoindoline-2-yl-carboxamido]-ethyl)-piperidine with a melting point of 138°-140° C. is obtained by hydrogenation with platinum oxide as catalyst.

By reaction of this product with sulfamide the 4-(2-[1-oxo-isoindoline-2-yl-carboxamido]-ethyl-1-piperidinesulfonamide with a melting point of 210°-212° C. is obtained.

The following compounds are obtained analogously: N-Butyl-N'-(4-[2-(1-oxo-isoindoline-2-yl-carboxamido)-ethyl]-piperidinesulfonyl)-urea melting point 154°-155° C. (from ethanol) N-(4-Methyl-cyclohexyl)-N'-(4-[2-(1-oxo-isoindoline-2-yl-carboxamido)-ethyl]-piperidinesulfonyl)-urea melting point 199°-200° C. (from ethanol) N-(4-Ethyl-cyclohexyl)-N'-(4-[2-(1-oxo-isoindoline-2-yl-carboxamido)-ethyl]-piperidinesulfonyl)-urea melting point 186°-187° C. (from ethanol) N-($\Delta^3$-Cyclohexenyl)-N'-(4-[2-(1-oxo-isoindoline-2-yl-carboxamido)-ethyl]-piperidinesulfonyl)-urea melting point 190°-191° C. (from ethanol) N-Bicyclo[2.2.1]hept-2-yl-methyl-N'-(4-[2-(1-oxo-isoindoline-2-yl-carboxamido)-ethyl]-piperidinesulfonyl)-urea melting point 167°-169° C. (from ethanol) N-Propyl-N'-(4-[2-(1-oxo-isoindoline-2-yl-carboxamido)-ethyl]-piperidinesulfonyl)-urea melting point 186°-187° C. (from ethanol) N-Benzyl-N'-(4-[2-(1-oxo-isoindoline-2-yl-carboxamido)-ethyl]-piperidinesulfonyl)-urea melting point 183°-184° C. (from ethanol-dimethylformamide) N-Cyclopentyl-N'-(4-[2-(1-oxo-isoindoline-2-yl-carboxamido)-ethyl]-piperidinesulfonyl)-urea melting point 172°-173° C. (from ethanol) N-Cycloheptyl-N'-(4-[2-(1-oxo-isoindoline-2-yl-carboxamido)-ethyl]-piperidinesulfonyl)-urea melting point 154°-155° C. (from ethanol) N-Cyclooctyl-N'-(4-[2-(1-oxo-isoindoline-2-yl-carboxamido)-ethyl]-piperidinesulfonyl)-urea melting point 151°-152° C. (from ethanol) N-Hexyl-N'-(4-[2-(1-oxo-isoindoline-2-yl-carboxamido)-ethyl]-piperidinesulfonyl)-urea melting point 133°-134° C. (from ethanol) N-Cyclopentyl-methyl-N'-(4-[2-(1-oxo-iso-indoline-2-yl-carboxamido)-ethyl]-piperidinesulfonyl)-urea melting point 169°-170° C. (from ethanol) N-Cyclobutyl-N'-(4-[2-(1-oxo-isoindoline-2-yl-carboxamido)-ethyl]-piperidinesulfonyl)-urea melting point 175°-177° C. (from ethanol) N-(4,4-Dimethyl-cyclohexyl)-N'-(4-[2-(1-oxo-isoindoline-2-yl-carboxamido)-ethyl]-piperidinesulfonyl)-urea melting point 171°-173° C. (from ethanol) N-(3-Methyl-Cyclopentylmethyl)-N'-(4-[2-(1-oxo-isoindoline-2-yl-carboxamido)-ethyl]-piperidinesulfonyl)-urea melting point 167°-168° C. (from ethanol)

EXAMPLE 2

N-(4-methoxy-cyclohexyl-N'-(4-[2-(1-oxo-isoindoline-2-yl-carboxamido)-ethyl]-piperidinesulfonyl)-urea 2.12 g of N-4-[2-(1-oxo-isoindoline-2-yl-carboxamido)-ethyl]-piperidinesulfonyl)-carbamic acid methyl ester (with a melting point of 170°-to 172° C., manufactured by reaction of 4-(2-[1-oxo-isoindoline-2-yl-carboxamido]-ethyl)-1-piperidinesulfonamide with chloroformic acid methyl ester) are stirred for 3 hours with 1.29 g of 4-methoxy-cyclohexylamine in 50 ml of dioxan under reflux. After cooling, the mixture is concentrated in vacuo, the residue is treated with dilute ammonia solution, filtered and acidified with 2 N hydrochloric acid. The product, first obtained in oily form, is extracted with chloroform, and the chloroform solution is evaporated after drying over sodium sulfate. The residue is recrystallized from ethyl acetate. The N-(4-methoxy-cyclohexyl)-N'-(4-[2-(1-oxo-isoindoline-2-yl-carboxamido)-ethyl]-piperidinesulfonyl)-urea thus obtained melts at 163°-164° C. The following compounds are obtained analogously: N-Bicyclo[2.2.1]hept-2-yl-N'-(4-[2-(1-oxo-isoindoline-2-yl-carboxamido)-ethyl]-piperidinesulfonyl)-urea melting point 145°-147° C. (from ethanol-dimethylformamide) N-($\Delta^3$-Cyclohexenyl-methyl)-N'-(4-[2-(1-oxo-isoindline-2-yl-carboxamido)-ethyl]-piperidinesulfonyl)-urea melting point 193°-195° C. (from ethanol-dimethylformamide) N-(Bicyclo[2.2.1]-hept-5-en-2-yl-methyl)-N'-(4-[2-(1-oxo-isoindoline-2-yl-carboxamido)-ethyl]-piperidinesulfonyl)-urea melting point 178°-180° C. (from ethanol) N-(4-Chloro-cyclohexyl)-N'-(4-[2-(1-oxo-isoindoline-2-yl-carboxamido)-ethyl]-piperidinesulfonyl)-urea melting point 199°-201° C. (from ethyl acetate).

EXAMPLE 3

N-cyclohexyl-N'-(4-[2-(1-oxo-isoindoline-2-yl-carboxamido)-ethyl]-piperidinesulfonyl)-urea 0.51 g of N-cyclohexyl-N'-(4-[2-(1-oxo-isoindoline-2-yl-carboxamido)-ethyl]-piperidinesulfonyl)-thiourea (melting point 165°-166° C., manufactured from the corresponding sulfonamide with cyclohexyl mustard oil) is heated for 4 hours in 25 ml of water and 25 ml of methanol with 0.21 g of yellow mercury oxide to 55°-60° C. (bath temperature). After cooling, the mercury sulfide in suction-filtered, the filtrate is concentrated and recrystallized from ethanol. The N-cyclohexyl-N'-(4-[2-(1-oxo-isoindoline-2-yl-carboxamido)-ethyl]-piperidinesulfonyl)-urea obtained melts at 175°-177° C.

EXAMPLE 4

N-cyclohexyl-N'-(4-[2-(1-oxo-isoindoline-2-yl-carboxamido)-ethyl]-piperidinesulfonyl)-urea 0.97 g of N-cyclohexyl-N'-(4-[2-(1-oxo-isoindoline-2-yl-carboxamido)-ethyl]-piperidinesulfonyl)-thiourea (melting point 165°-166° C., manufactured from the corresponding sulfonamide with cyclohexyl mustard oil) is heated to 50°-55° C. (bath temperature) for 6 hours in 30 ml of absolute methanol after addition of 0.32 g of mercury oxide. Subsequently, the product is cooled, filtered and evaporated in vacuo. The N-cyclohexyl-N'-(4-[2-(1-oxo-isoindoline-2-yl-carboxamido)-ethyl]-piperidinesulfonyl)-isourea methyl ether obtained as residue melts at 105°-107° C.

0.5 g of the isourea methyl ether manufactured in this way is stirred in 15 ml of concentrated hydrochloric acid for 2 hours at 50° C. After diluting with 20 ml of water the batch is suction-filtered and the N-cyclohexyl-N'-(4-[2-(1-oxo-isoindoline-2-yl-carboxamido)-ethyl]-piperidinesulfonyl)-urea is recrystallized from ethanol. The product melts at 174°-176° C. and shows no melting point depression, with a product prepared in another way.

EXAMPLE 5

N-cyclohexyl-N'-(4-[2-(1-oxo-3-methyl-isoindoline-2-yl-carboxamido)-ethyl]-piperidinesulfonyl)-urea 5.88 g of 1-oxo-3-methyl-isoindoline are stirred under reflux for 4 hours in 100 ml of absolute toluene with 1.92 g of a 55-60% sodium hydride dispersion. The cooled mixture is added in portions to 70 ml of an about 15% phosgene/toluene solution and heated to 40°-50° C. for another 2 hours. Subsequently, the inorganic precipitate is suction-filtered and the solution is concentrated. 1.2 g of the 1-oxo-3-methyl-isoindoline-2-carbamoyl-chloride so obtained are dissolved in 50 ml of methylene chloride and added dropwise at room temperature to a suspension of 2.4 g of N-(4-[2-aminoethyl]-piperidinesulfonyl)-N'-cyclohexyl urea in 50 ml of methylene chloride and 1.54 g of sodium carbonate in 15 ml of water. Stirring is continued for 3 hours at room temperature, and subsequently the product is acidified with 2 N HCl. The organic phase is separated, dried over $Na_2SO_4$ and concentrated in vacuo. The oily residue is once precipitated from dilute ammonia with dilute hydrochloric acid, and for final purification it is passed over a silica gel column (eluent: chloroform/methanol=20/1). The N-cyclohexyl-N'-(4-[1-oxo-3-methyl-isoindoline-2-yl-carboxamido)-ethyl]-piperidinesulfonyl)-urea thus obtained melts at 143°-145° C. and was recrystallized from ethanol.

The N-(4-[2-aminoethyl]-piperidinesulfonyl)-N'-cyclohexyl urea used as starting material was synthesized in the following way:

4-(Aminoethyl)-pyridine are reacted in methyl chloride with acetyl chloride. The 4-(2-[-acetylamino]-ethyl-pyridine thus obtained is hydrogenated in methanol after addition of ethanolic hydrochlorid acid, with platinum oxide as catalyst to give 4-(2-[acetylamino]-ethyl)-piperidine (oily). From this product, the 4-(2-[acetylamino]-ethyl)-piperidine-1-sulfonamide with the melting point of 205°-206° C. is obtained by reaction under reflux with sulfamide in pyridine. The N-(4-[2-acetyl-amino)-ethyl]-piperidinesulfonyl)-N'-cyclohexyl urea (melting point 175°-176° C.) from ethanol) is obtained from the sulfonamide by reaction with sodium carbonate and cyclohexyl isocyanate in butanone-(2), and by saponification with boiling aqueous sodium hydroxide solution it is converted into N-(4-[2-aminoethyl]-piperidinesulfonyl)-N'-cyclohexyl urea with a melting point of 218°-220° C.

What is claimed is:

1. Sulfonylurea of the formula

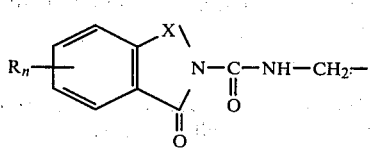

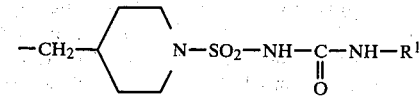

in which n is 1 or 2;

R is hydrogen, alkyl of 1 to 4 carbon atoms, alkoxy of 1 to 4 carbon atoms or halogen, the Rs being identical or different when n is 2;

X is —$CH_2$—, —$CH_2$—$CH_2$— or —$CH(CH_3)$—;

$R^1$ is alkyl of 2 to 8 carbon atoms, cycloalkyl, alkylcycloalkyl, dialkylcycloalkyl, cycloalkylalkyl, cycloalkenyl, or alkylcycloalkenyl, in each case with 5 to 9 carbon atoms, methylcyclopentylmethyl, cyclohexenylmethyl, chlorocyclohexyl, methoxycyclohexyl, bicyclo[2.2.1]-heptyl, bicyclo[2.2.1]-heptenyl, bicyclo[2.2.1]heptylmethyl, bicyclo[2.2.1]-heptenylmethyl, bicyclo[2.2.2]octyl, nortricyclyl, adamantyl or benzyl, or a physiologically acceptable salt thereof.

2. A compound as defined in claim 1 in which R is hydrogen, methyl, methoxy or chlorine, X is —$CH_2$— and $R^1$ is butyl, cyclohexyl or methylcyclohexyl.

3. The compound of claim 1 which is N-cyclohexyl-N'-(4-[2-(1-oxo-isoindoline-2-yl-carboxamido)-ethyl]-piperidinesulfonyl)-urea, or a physiologically acceptable salt thereof.

4. Antidiabetic composition containing a hypoglycemically effective amount of a sulfonylurea as defined in claim 1 and a pharmaceutically acceptable carrier therefor.

5. Antidiabetic composition containing a hypoglycemically effective amount of the sulfonylurea as defined in claim 3 and a pharmaceutically acceptable carrier therefor.

6. Method of treatment of diabetes which comprises oral administration to a diabetic patient of an effective amount of a compound as defined in claim 1.

7. Method of treatment of diabetes which comprises oral administration to a diabetic patient of an effective amount of the compound as defined in claim 3.

* * * * *